(12) United States Patent
Voguri et al.

(10) Patent No.: US 10,717,740 B2
(45) Date of Patent: Jul. 21, 2020

(54) SOLID FORMS OF ACALABRUTINIB AND PROCESS FOR PREPARATION THEREOF

(71) Applicant: DR. REDDY'S LABORATORIES LIMITED, Hyderabad (IN)

(72) Inventors: Raja Sekhar Voguri, Hyderabad (IN); Vishweshwar Peddy, Hyderabad (IN)

(73) Assignee: DR. REDDY'S LABORATORIES LIMITED., Hyderabad (IN)

( * ) Notice: Subject to any disclaimer, the term of this patent is extended or adjusted under 35 U.S.C. 154(b) by 0 days.

(21) Appl. No.: 16/620,039

(22) PCT Filed: Jun. 8, 2018

(86) PCT No.: PCT/IB2018/054146
§ 371 (c)(1),
(2) Date: Dec. 6, 2019

(87) PCT Pub. No.: WO2018/229613
PCT Pub. Date: Dec. 20, 2018

(65) Prior Publication Data
US 2020/0199130 A1     Jun. 25, 2020

(30) Foreign Application Priority Data

Jun. 13, 2017 (IN) .............................. 201741020641

(51) Int. Cl.
*C07D 487/04* (2006.01)

(52) U.S. Cl.
CPC ........ *C07D 487/04* (2013.01); *C07B 2200/13* (2013.01)

(58) Field of Classification Search
CPC ................................................... C07D 487/04
See application file for complete search history.

(56) References Cited

U.S. PATENT DOCUMENTS 9,796,721 B2   10/2017   Blatter et al.
2017/0029428 A1   2/2017   Blatter et al.

FOREIGN PATENT DOCUMENTS

WO     2013010868 A1     1/2013

OTHER PUBLICATIONS

International Search Report dated Oct. 23, 2018, for corresponding International Patent Application No. PCT/IB2018/054146.
Witten Opinion dated Oct. 23, 2018, for corresponding International Patent Application No. PCT/IB2018/054146.

*Primary Examiner* — Paul V Ward
(74) *Attorney, Agent, or Firm* — Pergament & Cepeda LLP; Milagros A. Cepeda; Edward D. Pergament (57) ABSTRACT

The present application relates to crystalline propylene glycol solvate of acalabrutinib and process for preparation thereof. The propylene glycol solvate of acalabrutinib may be selected from a group of racemic propylene glycol solvate, R-propylene glycol solvate and S-propylene glycol solvate of acalabrutinib. Specifically, the present application relates to crystalline forms RSV1, RSV2, RSV3 and RSV4 of acalabrutinib. Crystalline forms RSV2 and RSV3 are stable in all conditions and has excellent physico-chemical properties. The present application also relates to crystalline form RSVS of acalabrutinib.

12 Claims, 3 Drawing Sheets

SOLID FORMS OF ACALABRUTINIB AND PROCESS FOR PREPARATION THEREOF

This application is a National Stage Application under 35 U.S.C. § 371 of PCT International Application No. PCT/IB2018/054146, filed Jun. 8, 2018, which takes priority from Indian Provisional Application Number IN 201741020641, filed Jun. 13, 2017, all of which is herein incorporated by reference in their entirety.

FIELD OF INVENTION

The present application relates to crystalline forms of propylene glycol solvate of acalabrutinib. Specifically, the present application relates to crystalline forms RSV1, RSV2, RSV3 and RSV4 of acalabrutinib and process for preparation thereof. The present application also relates to crystalline form RSV5 of acalabrutinib and process for preparation thereof.

BACKGROUND OF INVENTION

The U.S. Pat. No. 9,796,721B2 (hereinafter referred as the U.S. '721 patent) discloses crystalline forms I, II, III, IV, V, VI, VII, VIII of acalabrutinib characterized by XRD. The U.S. '721 patent also discloses crystalline forms of acid addition salts of acalabrutinib, characterized by XRD.

In general, polymorphism refers to the ability of a substance to exist as two or more crystalline phases that have different spatial arrangements and/or conformations of molecules in their crystal lattices. Thus, "polymorphs" refer to different crystalline forms of the same pure substance in which the molecules have different spatial arrangements of the molecules, atoms, and/or ions forming the crystal. Different polymorphs may have different physical properties such as melting points, solubilities, etc. The variation in solid forms may appreciably influence the pharmaceutical properties, such as bioavailability, handling properties, dissolution rate, and stability, and in turn such properties can significantly influence the processing, shelf life, and commercial acceptance of a polymorphic form. For these reasons, regulatory authorities require drug manufacturing companies to put efforts into identifying all polymorphic forms, e.g., crystalline, amorphous, solvates, stable dispersions with a pharmaceutically acceptable carriers, etc., of new drug substances. The existence and possible numbers of polymorphic forms for a given compound cannot be predicted, and there are no "standard" procedures that can be used to prepare polymorphic forms of a substance. This is well-known in the art, as reported, for example, by A. Goho, "Tricky Business," Science News, Vol. 166(8), August 2004.

Hence, there remains a need for alternate polymorphic forms of acalabrutinib and processes for preparing them.

SUMMARY OF INVENTION

First aspect of the present application relates to crystalline propylene glycol solvate of acalabrutinib.

Second aspect of the present application relates to crystalline form RSV1 of acalabrutinib characterized by its powder X-ray diffraction (PXRD) pattern having peaks at about 7.99, 13.10 and 17.88±0.2° 2θ. In embodiments, the present application provides crystalline form RSV1 of acalabrutinib characterized by its PXRD pattern having additional peaks located at about 6.55, 9.93, 16.00, 18.79, 20.26, 21.73, 24.16 and 26.38±0.2° 2θ.

Figure 1:
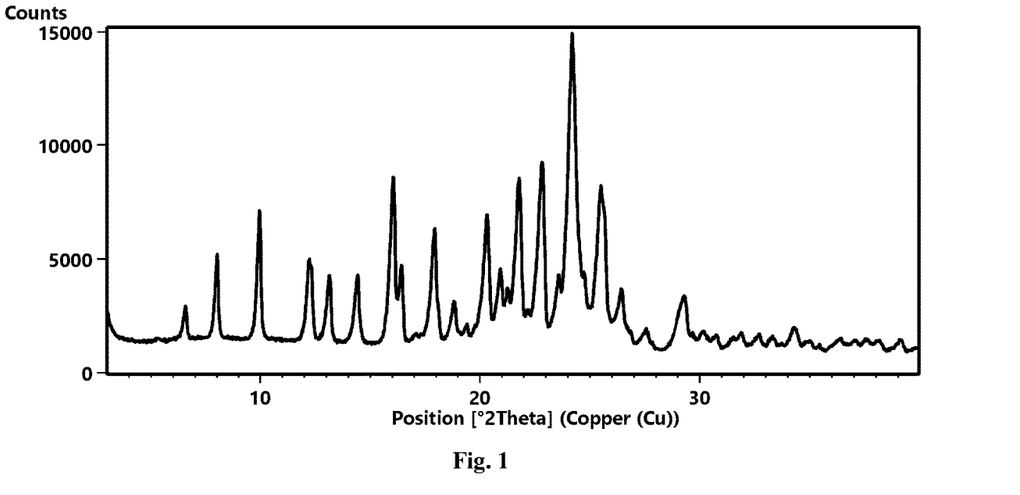
FIG. 1 is an illustration of a PXRD pattern of crystalline form RSV1 of acalabrutinib.

Third aspect of the present application relates to crystalline form RSV1 of acalabrutinib characterized by a PXRD pattern substantially as illustrated in FIG. 1.

Fourth aspect of the present application relates to a process for preparing crystalline form RSV1 of acalabrutinib comprising
a) mixing acalabrutinib and a solvent comprising propylene glycol;
b) optionally filtering the un-dissolved particles;
c) adding an anti-solvent;
d) isolating crystalline form RSV1 of acalabrutinib from the solution of step c); and
e) optionally drying the isolated product at suitable temperature.

Fifth aspect of the present application relates to a pharmaceutical composition comprising crystalline form RSV1 of acalabrutinib and one or more pharmaceutically acceptable excipient.

Sixth aspect of the present application relates to crystalline form RSV2 of acalabrutinib characterized by its powder X-ray diffraction (PXRD) pattern having peaks at about 5.14, 7.69, 12.23, 13.23, 17.08 and 29.00±0.2° 2θ. In embodiments, the present application relates to crystalline form RSV2 of acalabrutinib characterized by its PXRD pattern having additional peaks located at about 6.61, 10.66, 20.29, 21.22 and 22.94±0.2° 2θ.

Figure 2:
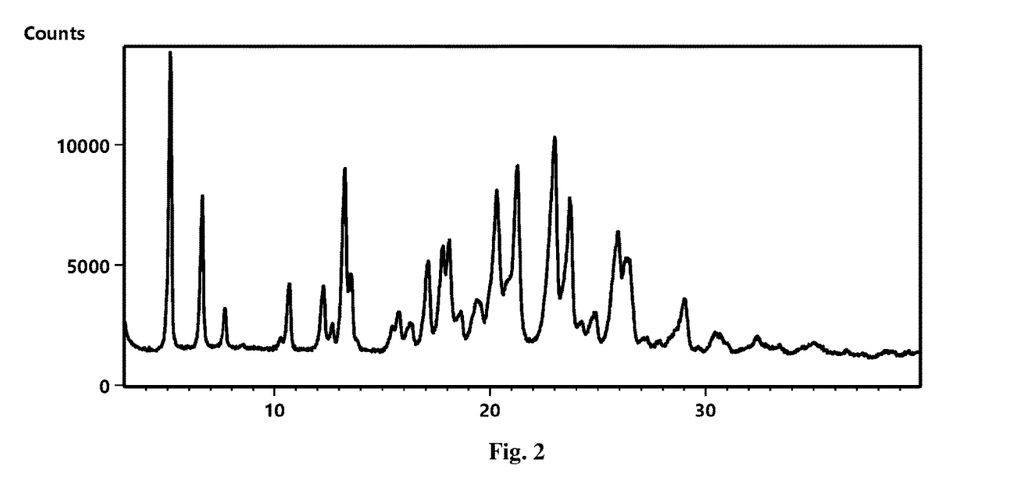
FIG. 2 is an illustration of a PXRD pattern of crystalline form RSV2 of acalabrutinib.

Seventh aspect of the present application relates to crystalline form RSV2 of acalabrutinib characterized by a PXRD pattern substantially as illustrated in FIG. 2.

Eighth aspect of the present application relates to a process for preparing crystalline form RSV2 of acalabrutinib comprising
a) mixing acalabrutinib and a solvent comprising R-propylene glycol;
b) optionally filtering the un-dissolved particles;
c) adding an anti-solvent;
d) isolating crystalline form RSV2 of acalabrutinib from the solution of step c); and
e) optionally drying the isolated product at suitable temperature.

Ninth aspect of the present application relates to a pharmaceutical composition comprising crystalline form RSV2 of acalabrutinib and one or more pharmaceutically acceptable excipient.

Tenth aspect of the present application relates to crystalline form RSV3 of acalabrutinib characterized by its powder X-ray diffraction (PXRD) pattern having peaks at about 7.99, 13.13, 16.03, 17.92 and 24.19±0.2° 2θ. In embodiments, the present application relates to crystalline form RSV3 of acalabrutinib characterized by its PXRD pattern having additional peaks located at about 9.93 and 18.85±0.2° 2θ.

Figure 3:
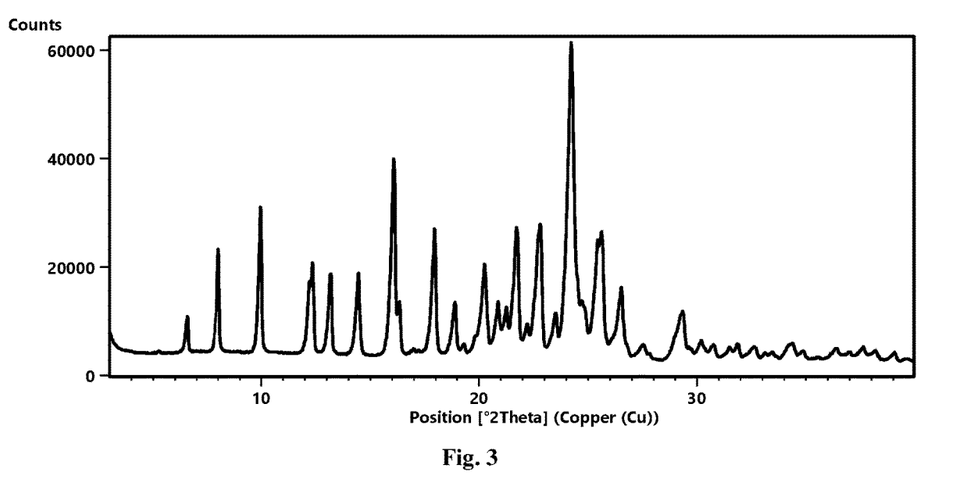
FIG. 3 is an illustration of a PXRD pattern of crystalline form RSV3 of acalabrutinib.

Eleventh aspect of the present application relates to crystalline form RSV3 of acalabrutinib characterized by a PXRD pattern substantially as illustrated in FIG. 3.

Twelfth aspect of the present application relates to a process for preparing crystalline form RSV3 of acalabrutinib comprising
a) mixing acalabrutinib and a solvent comprising S-propylene glycol;
b) optionally filtering the un-dissolved particles;
c) adding an anti-solvent;
d) isolating crystalline form RSV3 of acalabrutinib from the solution of step c); and
e) optionally drying the isolated product at suitable temperature.

Thirteenth aspect of the present application relates to a pharmaceutical composition comprising crystalline form RSV3 of acalabrutinib and one or more pharmaceutically acceptable excipient.

Fourteenth aspect of the present application relates to crystalline form RSV4 of acalabrutinib characterized by its powder X-ray diffraction (PXRD) pattern having peaks at about 5.11, 7.97, 13.13, 16.00, 17.87 and 24.12±0.2° 2θ. In embodiments, the present application provides crystalline form RSV4 of acalabrutinib characterized by its PXRD pattern having additional peaks located at about 6.56, 9.94, 18.78 and 20.29±0.2° 2θ.

Figure 4:
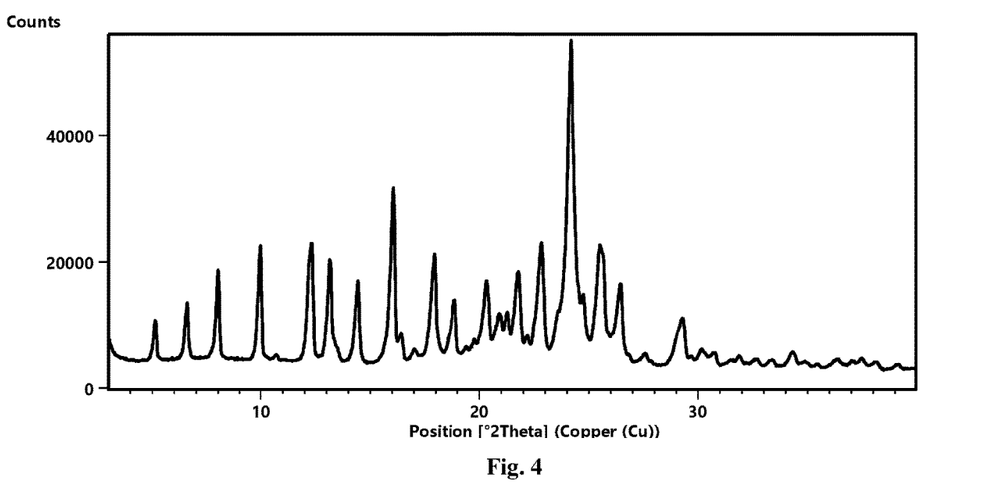
FIG. 4 is an illustration of a PXRD pattern of crystalline form RSV4 of acalabrutinib.

Fifteenth aspect of the present application relates to crystalline form RSV4 of acalabrutinib characterized by a PXRD pattern substantially as illustrated in FIG. 4.

Sixteenth aspect of the present application relates to a process for preparing crystalline form RSV4 of acalabrutinib comprising
a) mixing acalabrutinib and a solvent comprising propylene glycol;
b) optionally filtering the un-dissolved particles;
c) isolating crystalline form RSV4 of acalabrutinib from the solution of step b); and
d) optionally drying the isolated product at suitable temperature.

Seventeenth aspect of the present application relates to a pharmaceutical composition comprising crystalline form RSV4 of acalabrutinib and one or more pharmaceutically acceptable excipient.

Eighteenth aspect of the present application relates to crystalline form RSV5 of acalabrutinib characterized by its powder X-ray diffraction (PXRD) pattern having peaks at about 5.14 and 24.20±0.2° 2θ. In embodiments, the present application provides crystalline form RSV5 of acalabrutinib characterized by its PXRD pattern having additional peaks located at about 6.34, 10.31, 15.36, 20.94, 21.65 and 29.26±0.2° 2θ.

Figure 5:
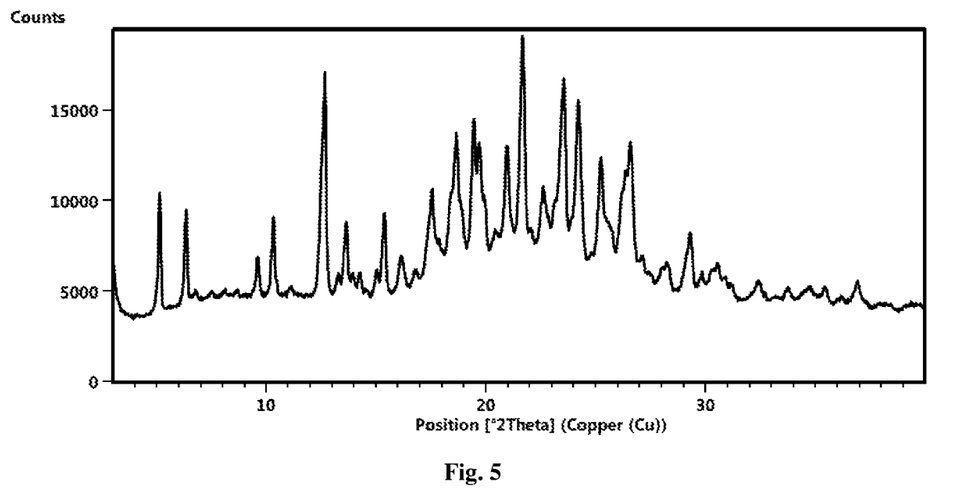
FIG. 5 is an illustration of a PXRD pattern of crystalline form RSV5 of acalabrutinib.

Nineteenth aspect of the present application relates to crystalline form RSV5 of acalabrutinib characterized by a PXRD pattern substantially as illustrated in FIG. 5.

Twentieth aspect of the present application relates to a process for preparing crystalline form RSV5 of acalabrutinib comprising
a) mixing acalabrutinib and a solvent comprising glycerol;
b) optionally drying the isolated product at suitable temperature.

Twenty first aspect of the present application relates to a pharmaceutical composition comprising crystalline form RSV5 of acalabrutinib and one or more pharmaceutically acceptable excipient.

DETAILED DESCRIPTION OF INVENTION

First aspect of the present application relates to crystalline propylene glycol solvate of acalabrutinib. In one embodiment, the crystalline propylene glycol solvate of acalabrutinib is a racemic propylene glycol solvate of acalabrutinib. In another embodiment, the crystalline propylene glycol solvate of acalabrutinib is a R-propylene glycol solvate of acalabrutinib. In yet another embodiment, the crystalline propylene glycol solvate of acalabrutinib is a S-propylene glycol solvate of acalabrutinib.

Second aspect of the present application relates to crystalline form RSV1 of acalabrutinib characterized by its powder X-ray diffraction (PXRD) pattern having peaks at about 7.99, 13.10 and 17.88±0.2° 2θ. In embodiments, the present application provides crystalline form RSV1 of acalabrutinib characterized by its PXRD pattern having additional peaks located at about 6.55, 9.93, 16.00, 18.79, 20.26, 21.73, 24.16 and 26.38±0.2° 2θ.

Third aspect of the present application relates to crystalline form RSV1 of acalabrutinib characterized by a PXRD pattern substantially as illustrated in FIG. 1.

In one embodiment, crystalline form RSV1 of acalabrutinib may be a propylene glycol solvate. The content of propylene glycol in crystalline form RSV1 of acalabrutinib may be in a range of about 2.0 to about 8.0% w/w. Specifically, the content of propylene glycol in crystalline form RSV1 of acalabrutinib may be in a range of about 4.0 to about 6.0% w/w.

Fourth aspect of the present application relates to a process for preparing crystalline form RSV1 of acalabrutinib comprising
a) mixing acalabrutinib and a solvent comprising propylene glycol;
b) optionally filtering the un-dissolved particles;
c) adding an anti-solvent;
d) isolating crystalline form RSV1 of acalabrutinib from the solution of step c); and
e) optionally drying the isolated product at suitable temperature.

In embodiments of step a), the solvent may be propylene glycol or a mixture of propylene glycol and an organic solvent. The organic solvent may include but not limited to, alcohols such as methanol, isopropanol and the like; ketones such as acetone, methyl isobutyl ketone and the like; ethers such as diethyl ether, tetrahydrofuran and the like; esters such as ethyl acetate, propyl acetate and the like. In a specific embodiment of step a), the solvent may be propylene glycol.

In one embodiment of step a), a mixture of acalabrutinib and a solvent comprising propylene glycol may be heated to dissolve acalabrutinib in the solvent. In a specific embodiment, a mixture of acalabrutinib and a solvent comprising propylene glycol may be heated at about 65° C. to about 75° C. to dissolve acalabrutinib in the solvent.

In one of the embodiments of step a), any physical form of acalabrutinib may be utilized, which may be crystalline or amorphous, for providing the solution of acalabrutinib in a solvent comprising propylene glycol. In another embodiment of step a), any physical form of acalabrutinib may be utilized, which may be anhydrous or hydrate, for providing the solution of acalabrutinib in a solvent comprising propylene glycol. Yet in another embodiment, any of the polymorphic forms as reported in the U.S. '721 patent may be used in step a). In a specific embodiment, crystalline Form III of acalabrutinib as reported in the U.S. '721 patent may be used in step a).

In one embodiment, the crystalline form RSV1 of acalabrutinib may optionally be added to the solution of acalabrutinib in a solvent comprising propylene glycol as seed crystals.

In embodiments of step c), the anti-solvent may include but not limited to, aliphatic hydrocarbon such hexane, heptane and the like; ethers such as diethyl ether, methyl tertiary butyl ether and the like; water. In a specific embodiment, the anti-solvent may be methyl tertiary butyl ether.

Isolation of crystalline form RSV1 of acalabrutinib in step d) may be performed by any technique known in the art. Specifically, crystalline form RSV1 of acalabrutinib may be isolated from the mixture of step c) by filtration. Optionally, the crystalline form RSV1 may be dried under suitable condition. Drying may suitably be carried out using any of an air tray dryer, vacuum tray dryer, fluidized bed dryer, spin flash dryer, flash dryer, and the like. The drying may be carried out at atmospheric pressure or above, or under reduced pressures, specifically at temperatures less than about 80° C. and more specifically less than about 60° C. and most specifically at 40° C. The drying may be carried out for any time period required for obtaining a desired product quality, such as from about 10 minutes to about 10 hours, or longer.

The crystalline form RSV1 of acalabrutinib may optionally be subjected to a particle size reduction procedure to produce desired particle sizes and distributions. Milling or micronization may be performed before drying, or after the completion of drying of crystalline form RSV1 of acalabrutinib. Equipment that may be used for particle size reduction includes but not limited to ball mill, roller mill, hammer mill, and jet mill.

The crystalline form RSV1 of acalabrutinib of the present application is stable and has excellent physico-chemical properties. The crystalline form RSV1 of acalabrutinib of the present application may be easily formulated into a pharmaceutical composition comprising acalabrutinib.

Fifth aspect of the present application relates to a pharmaceutical composition comprising crystalline form RSV1 of acalabrutinib and one or more pharmaceutically acceptable excipient.

Sixth aspect of the present application relates to crystalline form RSV2 of acalabrutinib characterized by its powder X-ray diffraction (PXRD) pattern having peaks at about 5.14, 7.69, 12.23, 13.23, 17.08 and 29.00±0.2° 2θ. In embodiments, the present application relates to crystalline form RSV2 of acalabrutinib characterized by its PXRD pattern having additional peaks located at about 6.61, 10.66, 20.29, 21.22 and 22.94±0.2° 2θ.

Seventh aspect of the present application relates to crystalline form RSV2 of acalabrutinib characterized by a PXRD pattern substantially as illustrated in FIG. 2.

In one embodiment, crystalline form RSV2 of acalabrutinib may be R-propylene glycol solvate. The content of R-propylene glycol in crystalline form RSV2 of acalabrutinib may be in a range of about 10.0 to about 22.0% w/w. Specifically, the content of R-propylene glycol in crystalline form RSV2 of acalabrutinib may be in a range of about 12.0 to about 20.0% w/w.

Eighth aspect of the present application relates to a process for preparing crystalline form RSV2 of acalabrutinib comprising
a) mixing acalabrutinib and a solvent comprising R-propylene glycol;
b) optionally filtering the un-dissolved particles;
c) adding an anti-solvent;
d) isolating crystalline form RSV2 of acalabrutinib from the solution of step c); and
e) optionally drying the isolated product at suitable temperature.

In embodiments of step a), the solvent may be R-propylene glycol or a mixture of R-propylene glycol and an organic solvent. The organic solvent may include but not limited to, alcohols such as methanol, isopropanol and the like; ketones such as acetone, methyl isobutyl ketone and the like; ethers such as diethyl ether, tetrahydrofuran and the like; esters such as ethyl acetate, propyl acetate and the like. In a specific embodiment of step a), the solvent may be R-propylene glycol.

In one embodiment of step a), a mixture of acalabrutinib and a solvent comprising R-propylene glycol may be heated to dissolve acalabrutinib in the solvent. In a specific embodiment, a mixture of acalabrutinib and a solvent comprising R-propylene glycol may be heated at about 60° C. to about 70° C. to dissolve acalabrutinib in the solvent.

In one of the embodiments of step a), any physical form of acalabrutinib may be utilized, which may be crystalline or amorphous, for providing the solution of acalabrutinib in a solvent comprising R-propylene glycol. In another embodiment of step a), any physical form of acalabrutinib may be utilized, which may be anhydrous or hydrate, for providing the solution of acalabrutinib in a solvent comprising R-propylene glycol. Yet in another embodiment, any of the polymorphic form as reported in the U.S. '721 patent may be used in step a). In a specific embodiment, crystalline Form III of acalabrutinib as reported in the U.S. '721 patent may be used in step a).

In one embodiment, the crystalline form RSV2 of acalabrutinib may optionally be added to the solution of acalabrutinib in a solvent comprising R-propylene glycol as seed crystals.

In embodiments of step c), the anti-solvent may include but not limited to, aliphatic hydrocarbon such hexane, heptane and the like; ethers such as diethyl ether, methyl tertiary butyl ether and the like; water. In a specific embodiment, the anti-solvent may be methyl tertiary butyl ether.

Isolation of crystalline form RSV2 of acalabrutinib in step d), may be performed by any technique known in the art. Specifically, crystalline form RSV2 of acalabrutinib may be isolated from the mixture of step c), by filtration. Optionally, the crystalline form RSV2 may be dried under suitable condition. Drying may be suitably carried out using any of an air tray dryer, vacuum tray dryer, fluidized bed dryer, spin flash dryer, flash dryer, and the like. The drying may be carried out at atmospheric pressure or above, or under reduced pressures, specifically at temperatures less than about 80° C. and more specifically less than about 60° C. and most specifically at 40° C. The drying may be carried out for any time period required for obtaining a desired product quality, such as from about 1 hour to about 10 hours, or longer.

The crystalline form RSV2 of acalabrutinib may optionally be subjected to a particle size reduction procedure to produce desired particle sizes and distributions. Milling or micronization may be performed before drying, or after the completion of drying of crystalline form RSV2 of acalabrutinib. Equipment that may be used for particle size reduction includes but not limited to ball mill, roller mill, hammer mill, and jet mill.

The crystalline form RSV2 of acalabrutinib of the present application is stable and has excellent physico-chemical properties. The crystalline form RSV2 of acalabrutinib of the present application may be easily formulated into a pharmaceutical composition comprising acalabrutinib.

In one embodiment, crystalline form RSV2 of acalabrutinib is found to be stable for 3 months in all conditions namely, at 40° C./75% RH; at 25° C./60% RH; and at 2-8° C.

Ninth aspect of the present application relates to a pharmaceutical composition comprising crystalline form RSV2 of acalabrutinib and one or more pharmaceutically acceptable excipient.

Tenth aspect of the present application relates to crystalline form RSV3 of acalabrutinib characterized by its powder X-ray diffraction (PXRD) pattern having peaks at about 7.99, 13.13, 16.03, 17.92 and 24.19±0.2° 2θ. In embodiments, the present application relates to crystalline form RSV3 of acalabrutinib characterized by its PXRD pattern having additional peaks located at about 9.93 and 18.85±0.2° 2θ.

Eleventh aspect of the present application relates to crystalline form RSV3 of acalabrutinib characterized by a PXRD pattern substantially as illustrated in FIG. 3.

In one embodiment, crystalline form RSV3 of acalabrutinib may be S-propylene glycol solvate. The content of S-propylene glycol in crystalline form RSV3 of acalabrutinib may be in a range of about 2.0 to about 8.0% w/w. Specifically, the content of S-propylene glycol in crystalline form RSV3 of acalabrutinib may be in a range of about 4.0 to about 6.0% w/w.

Twelfth aspect of the present application relates to a process for preparing crystalline form RSV3 of acalabrutinib comprising a) mixing acalabrutinib and a solvent comprising S-propylene glycol;
b) optionally filtering the un-dissolved particles;
c) adding an anti-solvent;
d) isolating crystalline form RSV3 of acalabrutinib from the solution of step c); and
e) optionally drying the isolated product at suitable temperature.

In embodiments of step a), the solvent may be S-propylene glycol or a mixture of S-propylene glycol and an organic solvent. The organic solvent may include but not limited to, alcohols such as methanol, isopropanol and the like; ketones such as acetone, methyl isobutyl ketone and the like; ethers such as diethyl ether, tetrahydrofuran and the like; esters such as ethyl acetate, propyl acetate and the like. In a specific embodiment of step a), the solvent may be S-propylene glycol.

In one embodiment of step a), a mixture of acalabrutinib and a solvent comprising S-propylene glycol may be heated to dissolve acalabrutinib in the solvent. In a specific embodiment, a mixture of acalabrutinib and a solvent comprising S-propylene glycol may be heated at about 45° C. to about 55° C. to dissolve acalabrutinib in the solvent.

In one of the embodiments of step a), any physical form of acalabrutinib may be utilized, which may be crystalline or amorphous, for providing the solution of acalabrutinib in a solvent comprising S-propylene glycol. In another embodiment of step a), any physical form of acalabrutinib may be utilized, which may be anhydrous or hydrate, for providing the solution of acalabrutinib in a solvent comprising S-propylene glycol. Yet in another embodiment, any of the polymorphic form as reported in the U.S. '721 patent may be used in step a). In a specific embodiment, crystalline Form III of acalabrutinib as reported in the U.S. '721 patent may be used in step a).

In one embodiment, the crystalline form RSV3 of acalabrutinib may optionally be added to the solution of acalabrutinib in a solvent comprising S-propylene glycol as seed crystals.

In embodiments of step c), the anti-solvent may include but not limited to, aliphatic hydrocarbon such hexane, heptane and the like; ethers such as diethyl ether, methyl tertiary butyl ether and the like; water. In a specific embodiment, the anti-solvent may be methyl tertiary butyl ether.

Isolation of crystalline form RSV3 of acalabrutinib in step d) may be performed by any technique known in the art. Specifically, crystalline form RSV3 of acalabrutinib may be isolated from the mixture of step c) by filtration. Optionally, the crystalline form RSV3 may be dried under suitable condition. Drying may be suitably carried out using any of an air tray dryer, vacuum tray dryer, fluidized bed dryer, spin flash dryer, flash dryer, and the like. The drying may be carried out at atmospheric pressure or above, or under reduced pressures, specifically at temperatures less than about 80° C. and more specifically less than about 60° C. and most specifically at 40° C. The drying may be carried out for any time period required for obtaining a desired product quality, such as from about 1 hour to about 20 hours, or longer.

The crystalline form RSV3 of acalabrutinib may optionally be subjected to a particle size reduction procedure to produce desired particle sizes and distributions. Milling or micronization may be performed before drying, or after the completion of drying of crystalline form RSV3 of acalabrutinib. Equipment that may be used for particle size reduction includes but not limited to ball mill, roller mill, hammer mill, and jet mill.

The crystalline form RSV3 of acalabrutinib of the present application is stable and has excellent physico-chemical properties. The crystalline form RSV3 of acalabrutinib of the present application may be easily formulated into a pharmaceutical composition comprising acalabrutinib.

In one embodiment, crystalline form RSV3 of acalabrutinib is found to be stable for 3 months in all conditions namely, at 40° C./75% RH; at 25° C./60% RH; and at 2-8° C.

Thirteenth aspect of the present application relates to a pharmaceutical composition comprising crystalline form RSV3 of acalabrutinib and one or more pharmaceutically acceptable excipient.

Fourteenth aspect of the present application relates to crystalline form RSV4 of acalabrutinib characterized by its powder X-ray diffraction (PXRD) pattern having peaks at about 5.11, 7.97, 13.13, 16.00, 17.87 and 24.12±0.2° 2θ. In embodiments, the present application provides crystalline form RSV4 of acalabrutinib characterized by its PXRD pattern having additional peaks located at about 6.56, 9.94, 18.78 and 20.29±0.2° 2θ.

Fifteenth aspect of the present application relates to crystalline form RSV4 of acalabrutinib characterized by a PXRD pattern substantially as illustrated in FIG. 4.

In one embodiment, crystalline form RSV4 of acalabrutinib may be propylene glycol solvate. The content of propylene glycol in crystalline form RSV4 of acalabrutinib may be in a range of about 10.0 to about 20.0% w/w. Specifically, the content of propylene glycol in crystalline form RSV4 of acalabrutinib may be in a range of about 12.0 to about 16.0% w/w.

Sixteenth aspect of the present application relates to a process for preparing crystalline form RSV4 of acalabrutinib comprising a) mixing acalabrutinib and a solvent comprising propylene glycol;
b) optionally filtering the un-dissolved particles;
c) isolating crystalline form RSV4 of acalabrutinib from the solution of step b); and
d) optionally drying the isolated product at suitable temperature.

In embodiments of step a), the solvent may be propylene glycol or a mixture of propylene glycol and an organic solvent. The organic solvent may include but not limited to, alcohols such as methanol, isopropanol and the like; ketones such as acetone, methyl isobutyl ketone and the like; ethers such as diethyl ether, tetrahydrofuran and the like; esters such as ethyl acetate, propyl acetate and the like. In a specific embodiment, the solvent may be propylene glycol.

In one embodiment of step a), a mixture of acalabrutinib and a solvent comprising propylene glycol may be heated to dissolve acalabrutinib in the solvent. In a specific embodiment, a mixture of acalabrutinib and a solvent comprising propylene glycol may be heated at about 60° C. to about 70° C. to dissolve acalabrutinib in the solvent.

In one of the embodiments of step a), any physical form of acalabrutinib may be utilized, which may be crystalline or amorphous, for providing the solution of acalabrutinib in a solvent comprising propylene glycol. In another embodiment of step a), any physical form of acalabrutinib may be utilized, which may be anhydrous or hydrate, for providing the solution of acalabrutinib in a solvent comprising propylene glycol. Yet in another embodiment, any of the polymorphic form as reported in the U.S. '721 patent may be used in step a). In a specific embodiment, crystalline Form III of acalabrutinib as reported in the U.S. '721 patent may be used in step a).

In one embodiment, the crystalline form RSV4 of acalabrutinib may optionally be added to the solution of acalabrutinib in a solvent comprising propylene glycol as seed crystals.

Isolation of crystalline form RSV4 of acalabrutinib in step c) may be performed by any technique known in the art. Isolation of crystalline form RSV4 of acalabrutinib in step c) may involve methods including crystallization, Evaporation, cooling, concentrating the mass, adding an anti-solvent, adding seed crystals to induce crystallization, or the like. Specifically, crystalline form RSV4 of acalabrutinib may be isolated from the mixture of step b) by cooling followed by filtration. In embodiments of step c) the reaction mixture may be cooled to about 20-30° C. Optionally, the crystalline form RSV4 may be dried under suitable condition. Drying may be suitably carried out using any of an air tray dryer, vacuum tray dryer, fluidized bed dryer, spin flash dryer, flash dryer, and the like. The drying may be carried out at atmospheric pressure or above, or under reduced pressures, specifically at temperatures less than about 80° C. and more specifically less than about 60° C. and most specifically at 40° C. The drying may be carried out for any time period required for obtaining a desired product quality, such as from about 10 minutes to about 10 hours, or longer.

The crystalline form RSV4 of acalabrutinib may optionally be subjected to a particle size reduction procedure to produce desired particle sizes and distributions. Milling or micronization may be performed before drying, or after the completion of drying of crystalline form RSV4 of acalabrutinib. Equipment that may be used for particle size reduction includes but not limited to ball mill, roller mill, hammer mill, and jet mill.

The crystalline form RSV4 of acalabrutinib of the present application is stable and has excellent physico-chemical properties. The crystalline form RSV4 of acalabrutinib of the present application may be easily formulated into a pharmaceutical composition comprising acalabrutinib.

Seventeenth aspect of the present application relates to a pharmaceutical composition comprising crystalline form RSV4 of acalabrutinib and one or more pharmaceutically acceptable excipient.

Eighteenth aspect of the present application relates to crystalline form RSV5 of acalabrutinib characterized by its powder X-ray diffraction (PXRD) pattern having peaks at about 5.14 and 24.20±0.2° 2θ. In embodiments, the present application provides crystalline form RSV5 of acalabrutinib characterized by its PXRD pattern having additional peaks located at about 6.34, 10.31, 15.36, 20.94, 21.65 and 29.26±0.2° 2θ.

Nineteenth aspect of the present application relates to crystalline form RSV5 of acalabrutinib characterized by a PXRD pattern substantially as illustrated in FIG. 5.

Twentieth aspect of the present application relates to a process for preparing crystalline form RSV5 of acalabrutinib comprising
a) mixing acalabrutinib and a solvent comprising glycerol;
b) optionally drying the isolated product at suitable temperature.

In embodiments of step a), the solvent may be glycerol or a mixture of glycerol and an organic solvent. The organic solvent may include but not limited to, alcohols such as methanol, isopropanol and the like; ketones such as acetone, methyl isobutyl ketone and the like; ethers such as diethyl ether, tetrahydrofuran and the like; esters such as ethyl acetate, propyl acetate and the like. In a specific embodiment, the solvent may be glycerol.

In one embodiment of step a), a mixture of acalabrutinib and a solvent comprising glycerol may be heated. In a specific embodiment, a mixture of acalabrutinib and a solvent comprising glycerol may be heated at about 50° C. to about 70° C.

In one of the embodiments of step a), any physical form of acalabrutinib may be utilized, which may be crystalline or amorphous, for providing the solution of acalabrutinib in a solvent comprising propylene glycol. In another embodiment of step a), any physical form of acalabrutinib may be utilized, which may be anhydrous or hydrate, for providing the solution of acalabrutinib in a solvent comprising propylene glycol. Yet in another embodiment, any of the polymorphic form as reported in the U.S. '721 patent may be used in step a).

Drying the crystalline form RSV5 of step b), may be suitably carried out using any of an air tray dryer, vacuum tray dryer, fluidized bed dryer, spin flash dryer, flash dryer, and the like. The drying may be carried out at atmospheric pressure or above, or under reduced pressures, specifically at temperatures less than about 80° C. and more specifically less than about 60° C. and most specifically at 45° C. The drying may be carried out for any time period required for obtaining a desired product quality, such as from about 10 minutes to about 10 hours, or longer.

The crystalline form RSV5 of acalabrutinib may optionally be subjected to a particle size reduction procedure to produce desired particle sizes and distributions. Milling or micronization may be performed before drying, or after the completion of drying of crystalline form RSV5 of acalabrutinib. Equipment that may be used for particle size reduction includes but not limited to ball mill, roller mill, hammer mill, and jet mill.

The crystalline form RSV5 of acalabrutinib of the present application is stable and has excellent physico-chemical properties. The crystalline form RSV5 of acalabrutinib of the present application may be easily formulated into a pharmaceutical composition comprising acalabrutinib.

Twenty first aspect of the present application relates to a pharmaceutical composition comprising crystalline form RSV5 of acalabrutinib and one or more pharmaceutically acceptable excipient.

Yet another aspect of the present application relates to a pharmaceutical composition comprising crystalline form RSV1 of acalabrutinib or crystalline form RSV2 of acalabrutinib or crystalline form RSV3 of acalabrutinib or crystalline form RSV4 of acalabrutinib or crystalline form RSV5 of acalabrutinib and one or more pharmaceutically acceptable excipient. Crystalline form RSV1 of acalabrutinib or crystalline form RSV2 of acalabrutinib or crystalline form RSV3 of acalabrutinib or crystalline form RSV4 of acalabrutinib or crystalline form RSV5 of acalabrutinib together with one or more pharmaceutically acceptable excipients of the present application may be formulated as: solid oral dosage forms such as, but not limited to, powders, granules, pellets, tablets, and capsules; liquid oral dosage forms such as, but not limited to, syrups, suspensions, dispersions, and emulsions; and injectable preparations such as, but not limited to, solutions, dispersions, and freeze dried compositions. Formulations may be in the forms of immediate release, delayed release, or modified release. Further, immediate release compositions may be conventional, dispersible, chewable, mouth dissolving, or flash melt preparations, and modified release compositions that may comprise hydrophilic or hydrophobic, or combinations of hydrophilic and hydrophobic, release rate controlling substances to form matrix or reservoir or combination of matrix and reservoir systems. The compositions may be prepared using any one or more of techniques such as direct blending, dry granulation, wet granulation, and extrusion and spheronization. Compositions may be presented as uncoated, film coated, sugar coated, powder coated, enteric coated, and modified release coated.

Pharmaceutically acceptable excipients that are useful in the present application include, but are not limited to: diluents such as starches, pregelatinized starches, lactose, powdered celluloses, microcrystalline celluloses, dicalcium phosphate, tricalcium phosphate, mannitol, sorbitol, sugar, and the like; binders such as acacia, guar gum, tragacanth, gelatin, polyvinylpyrrolidones, hydroxypropyl celluloses, hydroxypropyl methyl celluloses, pregelatinized starches, and the like; disintegrants such as starches, sodium starch glycolate, pregelatinized starches, crospovidones, croscarmellose sodium, colloidal silicon dioxide, and the like; lubricants such as stearic acid, magnesium stearate, zinc stearate, and the like; glidants such as colloidal silicon dioxide and the like; solubility or wetting enhancers such as anionic, cationic, or neutral surfactants; complex forming agents such as various grades of cyclodextrins and resins; and release rate controlling agents such as hydroxypropyl celluloses, hydroxymethyl celluloses, hydroxypropyl methylcelluloses, ethylcelluloses, methylcelluloses, various grades of methyl methacrylates, waxes, and the like. Other pharmaceutically acceptable excipients that are useful include, but are not limited to, film formers, plasticizers, colorants, flavoring agents, sweeteners, viscosity enhancers, preservatives, antioxidants, and the like.

X-ray powder diffractograms of form RSV1, RSV2, RSV3, RSV4 and RSV5 are recorded on PANalytical X'Pert PRO diffractometer equipped with X'Celerator detector using generator setting of 45 mA and 40 kV at room temperature with X-ray source of copper (1.5406 Å). The diffractograms were collected over a 2θ range of 3-40°.

DEFINITIONS

The following definitions are used in connection with the present application unless the context indicates otherwise.

The terms "about," "general, 'generally," and the like are to be construed as modifying a term or value such that it is not an absolute. Such terms will be defined by the circumstances and the terms that they modify as those terms are understood by those of skill in the art. This includes, at very least, the degree of expected experimental error, technique error and instrument error for a given technique used to measure a value.

A name used herein to characterize a crystalline form should not be considered limiting with respect to any other substance possessing similar or identical physical and chemical characteristics, but rather it should be understood that these designations are mere identifiers that should be interpreted according to the characterization information also presented herein.

All percentages and ratios used herein are by weight of the total composition and all measurements made are at about 25° C. and about atmospheric pressure, unless otherwise designated. All temperatures are in degrees Celsius unless specified otherwise. As used herein, the terms "comprising" and "comprises" mean the elements recited, or their equivalents in structure or function, plus any other element or elements which are not recited. The terms "having" and "including" are also to be construed as open ended. All ranges recited herein include the endpoints, including those that recite a range between two values. Whether so indicated or not, all values recited herein are approximate as defined by the circumstances, including the degree of expected experimental error, technique error, and instrument error for a given technique used to measure a value.

The term "optional" or "optionally" is taken to mean that the event or circumstance described in the specification may or may not occur, and that the description includes instances where the event occurs and instances where it does not.

In general, a diffraction angle (2θ) in powder X-ray diffractometry may have an error in the range of ±0.2°. Therefore, the aforementioned diffraction angle values should be understood as including values in the range of about ±0.2°. Accordingly, the present application includes not only crystals whose peak diffraction angles in powder X-ray diffractometry completely coincide with each other, but also crystals whose peak diffraction angles coincide with each other with an error of about ±0.2°. Therefore, in the present specification, the phrase "having a diffraction peak at a diffraction angle (2θ±0.2°) of 19.6°" means "having a diffraction peak at a diffraction angle (2θ) of 19.4 to 19.8. Although the intensities of peaks in the x-ray powder diffraction patterns of different batches of a compound may vary slightly, the peaks and the peak locations are characteristic for a specific polymorphic form. The relative intensities of the XRD peaks can vary depending on the sample preparation technique, crystal size distribution, various filters used, the sample mounting procedure, and the particular instrument employed. Moreover, instrument variation and other factors can affect the 2-theta values.

Certain specific aspects and embodiments of the present application will be explained in greater detail with reference to the following examples, which are provided only for purposes of illustration and should not be construed as limiting the scope of the disclosure in any manner.

EXAMPLES

Example 1: Preparation of Crystalline Form RSV1 of Acalabrutinib

A mixture of crystalline Form III of acalabrutinib (1 g) as reported in U.S. '721 patent and propylene glycol (1.4 mL) was heated to 70° C. and stirred for about 60 min at the same temperature. A clear solution was observed. Methyl tertiary butyl ether (20 mL) was added to the above clear solution at 70° C. The above reaction mass was cooled to 25° C. and stirred for about 90 minutes at the same temperature. The precipitated solid was filtered under vacuum at 25° C. The resulting wet solid was dried in vacuum tray dryer (VTD) at 40° C. for about 18 hours to afford the title compound.
Propylene glycol content (By Chiral HPLC method): 5.40% w/w (S:R::82:18)

Example 2: Preparation of Crystalline Form RSV2 of Acalabrutinib

A mixture of crystalline Form III of acalabrutinib (1 g) as reported in U.S. '721 patent and R-propylene glycol (1.4 mL) were heated to 65° C. and stirred for about 30 min. The resulting clear solution was cooled to 25° C. Methyl tertiary butyl ether (6 mL) was added to the above solution at 25° C. and stirred for about 6 h at the same temperature. The precipitated solid was filtered under vacuum at 25° C. The resulting wet solid was dried using vacuum tray dryer (VTD) at about 40° C. for about 6 hours to afford the title compound.
Propylene glycol content (By Chiral HPLC method): 17.81% w/w (R:S::99.6:0.4)

Example 3: Preparation of Crystalline Form RSV3 of Acalabrutinib

A mixture of crystalline Form III of acalabrutinib (1 g) as reported in U.S. '721 patent and S-propylene glycol (1.4 mL) was heated to 50° C. and stirred for about 20 min. Methyl tertiary butyl ether (40 mL) was added to the above solution at 50° C. and stirred for about 20 minutes at the same temperature. The above reaction mass was cooled to 25° C. and stirred for 15 minutes. The reaction mass was kept at 25° C. for 30 minutes, solid was filtered under vacuum at 25° C. The resulting wet solid was dried using vacuum tray dryer (VTD) at about 40° C. for about 6 hours to afford the title compound.
Propylene glycol content (By Chiral HPLC method): 5.43% w/w (S:R::96.8::3.2)

Example 4: Preparation of Crystalline Form RSV4 of Acalabrutinib

A mixture of crystalline Form III of acalabrutinib (1 g) as reported in U.S. '721 patent and propylene glycol (1.4 mL) was heated to 65° C. and stirred for about 60 min at the same temperature. A clear solution was observed. The above reaction mass was cooled to 25° C. and stirred for about 60 minutes at the same temperature. The reaction mass was kept at 25° C. for 30 minutes. The resulting wet and sticky mass was dried in vacuum tray dryer (VTD) at 40° C. for about 5 hours to afford the title compound.
Propylene glycol content (By Chiral HPLC method): 13.96% w/w (S:R::47:53)

Example 5: Preparation of Crystalline Form RSV5 of Acalabrutinib

A mixture of acalabrutinib (1 g) and glycerol (0.8 mL) was heated to 60° C. and stirred for about 60 min at the same temperature. The above reaction mass was slowly cooled to 25° C. The resulting material was dried in vacuum tray dryer (VTD) at 45° C. for about 16 hours to afford the title compound.

We claim:

1. The crystalline form of acalabrutinib characterized by its powder X-ray diffraction (PXRD) pattern having peaks at about 5.14, 7.69, 12.23, 13.23, 17.08 and 29.00±0.2° 2θ.

2. The crystalline form of claim 1, further characterized by its powder X-ray diffraction (PXRD) pattern having additional peaks located at about 6.61, 10.66, 20.29, 21.22 and 22.94±0.2° 2θ.

3. The crystalline form of claim 1, further characterized by its powder X-ray diffraction (PXRD) pattern substantially as illustrated in FIG. 2.

4. The crystalline form of claim 1, wherein the crystalline form is crystalline R-propylene glycol solvate.

5. A process for preparing crystalline form of acalabrutinib of claim 1, comprising
   a) mixing acalabrutinib and a solvent comprising R-propylene glycol;
   b) optionally filtering the un-dissolved particles;
   c) adding an anti-solvent;
   d) isolating crystalline form of acalabrutinib from the solution of step c); and
   e) optionally drying the isolated product at suitable temperature.

6. The process of claim 5, wherein the anti-solvent of step c) is methyl tertiary butyl ether.

7. The crystalline form of acalabrutinib characterized by its powder X-ray diffraction (PXRD) pattern having peaks at about 7.99, 13.13, 16.03, 17.92 and 24.19±0.2° 2θ.

8. The crystalline form of claim 7, further characterized by its powder X-ray diffraction (PXRD) pattern having additional peaks located at about 9.93 and 18.85±0.2° 2θ.

9. The crystalline form of claim 7, further characterized by its powder X-ray diffraction (PXRD) pattern substantially as illustrated in FIG. 3.

10. The crystalline form of claim 7, wherein the crystalline form is crystalline S-propylene glycol solvate.

11. A process for preparing crystalline form of acalabrutinib of claim 7, comprising
    a) mixing acalabrutinib and a solvent comprising S-propylene glycol;
    b) optionally filtering the un-dissolved particles;
    c) adding an anti-solvent;
    d) isolating crystalline form of acalabrutinib from the solution of step c); and
    e) optionally drying the isolated product at suitable temperature.

12. The process of claim 11, wherein the anti-solvent of step c) is methyl tertiary butyl ether.

* * * * *